United States Patent [19]

Blanchet et al.

[11] Patent Number: 5,154,180
[45] Date of Patent: Oct. 13, 1992

[54] METHOD AND DEVICE FOR DETERMINING A SUBJECT'S SLEEP STATE BY PROCESSING AN ELECTROENCEPHALOGRAPHIC SIGNAL

[75] Inventors: Gérard Blanchet, Ivry sur Seine; Jacques Prado, Egly, both of France

[73] Assignee: France Telecom, Paris, France

[21] Appl. No.: 645,561

[22] Filed: Jan. 24, 1991

[30] Foreign Application Priority Data

Jan. 24, 1990 [FR] France .................... 90 00796

[51] Int. Cl.⁵ .................... A61B 5/0476
[52] U.S. Cl. .................... 128/731; 364/413.05
[58] Field of Search ........ 128/731; 364/413.05

[56] References Cited

U.S. PATENT DOCUMENTS

| | | | |
|---|---|---|---|
| 4,201,224 | 5/1980 | John | 128/731 |
| 4,214,591 | 7/1980 | Sato et al. | 128/731 |
| 4,616,333 | 10/1986 | Shimoni | 364/413.05 |
| 4,979,110 | 12/1990 | Albrecht et al. | 364/413.05 |
| 4,999,772 | 3/1991 | Bowman et al. | 364/413.05 |

FOREIGN PATENT DOCUMENTS

306346 3/1989 European Pat. Off.

OTHER PUBLICATIONS

Lacroix et al., "New Algorithms for On-Line Automatic Sleep Scoring, and Their Application to Mini and Micro-Computer", Journal A, vol. 26, No. 2, Apr. 1985 pp. 91-97.
Rosenfalck et al., "On-Line Analysis of EEG", IEEE-/Engineering in Medicine and Biology Society, pp. 418-422.
Principe, "SAMICOS—A Sleep Analyzing Microcomputer System" IEEE Transactions on Biomedical Engineering, vol. BME-33, No. 10, Oct. 1986, pp. 935-941.

Primary Examiner—William E. Kamm
Attorney, Agent, or Firm—Oliff & Berridge

[57] ABSTRACT

An electroencephalographic signal processing method allows the stages of sleep to be determined in real time as an EEG signal is being picked up. The EEG signal is divided into time segments of the same length; each signal segment is sampled digitally to obtain successive blocks of N samples; for each block i, M standardized correlation coefficients $R_{i,k}$ are determined, M being much far smaller than N; for each block i, the distances $D(i,j)$ between the coefficients $R_{i,k}$ of the current block and the coefficients $R_{j,k}$ of the centers of gravity of existing classes j are calculated; the minimum $D(i,p)$ of distances $D(i,j)$ is selected; block i is assigned to class p and the center of gravity of the class is updated if $D(i,p)$ is below a given threshold, while a new class is created if $D(i,p)$ is above the given threshold; and each class is assigned to the closest stage from the standpoint of energy distribution beween frequency bands.

6 Claims, 2 Drawing Sheets

METHOD AND DEVICE FOR DETERMINING A SUBJECT'S SLEEP STATE BY PROCESSING AN ELECTROENCEPHALOGRAPHIC SIGNAL

BACKGROUND OF THE INVENTION

Technical field

The invention relates to real-time processing of an electroencephalographic signal, generally called an EEG signal, with a view to automatic classification of a patient's sleep stages from the characteristics of the EEG signal. It has important, although not exclusive, applications in sleep studies in hospital laboratories, and in studying changes in sleeping patterns under drugs in pharmaceutical laboratories.

EEG specialists usually recognize six different stages, and the signals obtained in, successive time segments are allocated to one of the six stages.

At the present time, the successive sleep stages of a patient are determined by visually analyzing an EEG graph and that requires two to three days of work for each graph for one night of sleep, with a match of about 80% between the results obtained by different operators. This method of analysis is laborious and very slow. For each signal segment, the operator must make a frequency analysis by observing a time signal, implying considerable smoothing and subjective evaluation, which has led to the classification into six stages only, usually called waking, paradoxical sleep, stage 1, stage 2, stage 3, and stage 4.

A system has been proposed comprising a microcomputer which determines the sleep stages by analyzing signals from various leads of an electroencephalograph. The signals, sampled at a high frequency (1000 Hz for processing signals having a maximum frequency of 30 Hz) and digitized, are applied to a bank of digital filters with fixed characteristic frequencies. This device transposes visual analysis and does not improve the performance thereof.

SUMMARY OF THE INVENTION

It is an object of the invention to provide an improved method and device for processing an EEG signal; it is a more specific object to allow fully automatic classification of the successive time segments of the signal in real time, with a degree of agreement with visual classification that is of the same order of magnitude as between visual classifications conducted by different operators. It is a further object to provide a method that, where appropriate, allows far more detailed analysis and classification than direct observation methods.

With such objects in mind, the invention employs a self-learning technique that makes no starting hypothesis as to the particular characteristics of the EEG signal processed.

More precisely, there is provided a real-time processing method including the steps of: dividing an EEG signal into time segments of the same length; sampling each signal segment and digitizing the samples to obtain successive blocks of N samples; for each block i, determining M standardized correlation coefficients $R_{i,k}$ wherein M is far less than N; for each block i, computing the distances $D(i, j)$ between the coefficients $R_{i,k}$ of the current block and the coefficients $R_{j,k}$ of the centers of gravity of existing classes j; selecting the minimum $D(i,p)$ of distances $D(i,j)$, and assigning block i to class p if $D(i,p)$ is below a given threshold, updating the center of gravity of the class, while creating a new class if $D(i,p)$ is greater than the predetermined threshold.

It has been found experimentally that a single EEG channel, advantageously the vertex-occipital lead, is sufficient for making the classification, which reduces the volume of calculation to the point where a single minicomputer can analyze the EEG signals coming from several paths simultaneously.

In practice, good results, leading to an 80% match with visual analyses, have been obtained with sampling at 100 Hz, $N=3000$ (corresponding to 30-second segments), and $M=16$.

The invention also provides a system for implementing the above-defined method, comprising:
  an acquisition channel with a low pass or passband filter,
  a sampler and an analog-digital converter,
  a preprocessing microprocessor programmed to calculate correlation coefficients $R_{i,k}$ for each EEG signal segment, and
  a minicomputer for storing signal blocks and/or correlation coefficients, creating signal classes, assigning blocks, and updating the classes.

The acquisition channel can typically have a filter with a passband from 1 to 40 Hz (in the case of a 100 Hz sampler), possibly an analog multiplexer allowing several EEG signals to be processed, and a 12-bit analog-digital converter. The microprocessor preprocessing the data in real time can then be of the 16-bit type, designed to transmit the correlation coefficients to the minicomputer in 150 byte blocks after preprocessing of each block. The minicomputer can be a personal computer processing the data in real time and storing the definitive results, and possibly intermediate results, in a mass memory.

The invention will be better understood by reading the following description of a method constituting a particular embodiment of the invention, and a system for its implementation. The description refers to the accompanying drawings.

DETAILED DESCRIPTION OF A PREFERRED EMBODIMENT

Figure 1:
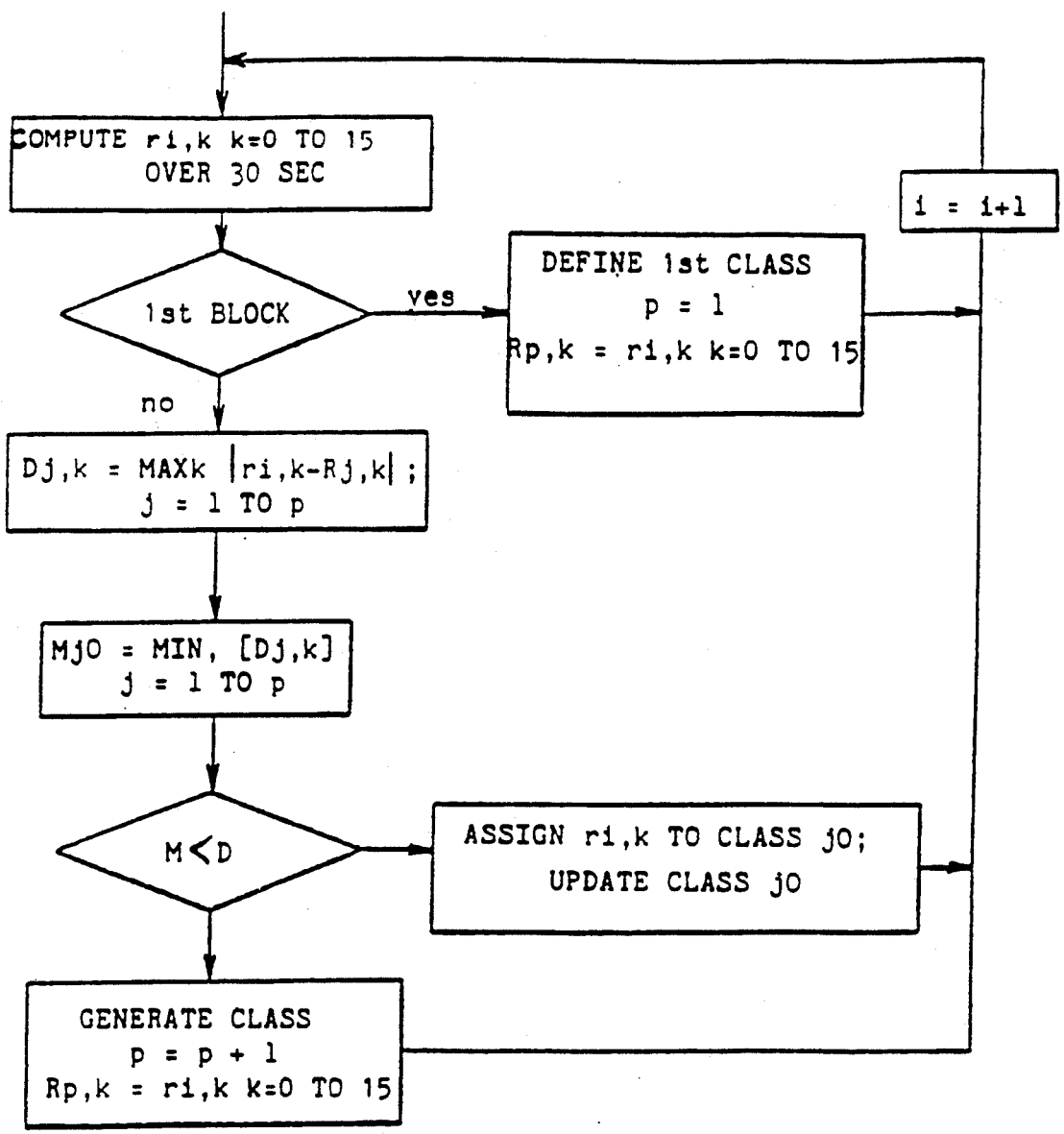
FIG. 1 is a flowchart of the preprocessing and classification stages of the method.

The part of the method which is implemented in real time may be considered as comprising:
  an EEG signal acquisition step;
  a preprocessing step; and
  a classification step, which can be supplemented by a delayed-time analysis.

Acquisition involves detection and amplification of an EEG signal, advantageously the vertex-occipital signal, and analog amplification to a level allowing the effect of noise to be reduced. The amplified signal is filtered in a band considered to be significant, usually 1 to 40 Hz. However, it is possible to use a narrower band, limited for example to 30 Hz. The signal is sampled at a frequency at least twice the upper limit of the filter band, e.g. 100 Hz. The samples are subjected to analog-digital conversion with a sufficient number of quantification levels to achieve the desired selectivity. In practice, 12-bit quantification, compatible with the use of a 16-bit microprocessor, will generally be satisfactory.

The samples go through the preprocessing stage and can also be stored in a mass memory allowing delayed-time processing and additional analysis.

During preprocessing, several signal self-correlation coefficients are calculated for the successive blocks of several thousands of samples. In practice, in the case of a sampling frequency of 100 Hz, 30-second segments may be used, containing N=3000 samples, and each sample of order i can be characterized by 16 correlation coefficients corresponding to time lags equal to the sampling rate. Thus, for the ith-order segment, there are 16 coefficients:

$$R_{i,k} = (1/N) \sum_{n=1}^{N} S_n S_{n+k} \tag{1}$$

where k varies from 0 to 15 for each block of N samples.

The classification is done iteratively, with the system learning as the experiment, lasting 8 to 10 hours, progresses. The iterative method allows signal block distribution classes to be created automatically, the blocks to be assigned to classes, and the classes to be adjusted. It uses a resemblance criterion based on a Chebyshev distance, applied not to the $R_{i,k}$ coefficients of formula (1), but to standardized coefficients $R^*$:

$$R^*_{i,k} = R_{i,k}/R_{i,0} \tag{2}$$

For greater simplicity, the standardized coefficients will be designated by the simple notation R, and not $R^*$. Coefficient $R^*_{i,0}$ is always equal to unity, coefficient $R_{i,0}$ is retained and represents the energy of signal segment i.

As a significant parameter for evaluating the resemblance between a signal segment and the typical segment of a pre-existing class, a distance consisting of the greatest of the fifteen differences each between one of the correlation coefficients of the signal of the current segment and the center of gravity of the corresponding coefficients of the segments already assigned to pre-existing classes, is used.

Distance D(i,j) considered to be significant for evaluating the resemblance between the ith-order segment of the EEG signal and each class j among the pre-existing classes is:

$$D(i,j) = MAX_k |R_{i,k} - R_{j,k}| \tag{3}$$

Then, that coefficient D(i,j) is determined, the number of said coefficients being equal to that of the pre-existing classes, which is the lowest for segment i of the signal considered. This minimum value $$D(i,p) = MIN_j D(i,j) \tag{4}$$

reveals the pre-existing class p for which there is the greatest resemblance to the signal segment of order i.

A test is then performed by comparing D(i,p) with a threshold D0 settable by the operator. If D(i,p) is less than the threshold, the sample block of order i (or signal segment i) is considered to belong to class p and the center of gravity of the coefficients in class p is updated by the operation:

$$R_{p,k} = [1/(N_p+1)] (N_p R_{p,k} + R_{i,k})$$

$$N_p = N_p + 1 \tag{5}$$

If, on the other hand, D(i,p) is greater than D0, a new class is created whose current block is the first block.

This threshold D0 is chosen as a function of the result of experiments for each individual system.

It is selected high enough for the number of classes generated in the course of the entire experiment not to be excessive and out of proportion to the number of sleep stages that visual analysis can distinguish, in order to ensure consistency with visual analysis. It must not be too small, as the number of classes would then be insufficient. The most appropriate value can be chosen by experiment. Once this value has been chosen for a given system, it is no longer necessary to modify it according to the patient.

It can be seen that the method initializes itself: it is sufficient to select the value of threshold D. The first block constitutes a first class which can be considered to be class 0 and the 16 correlation coefficients $R_{0,k}$ which serve as $R_{j,k}$ comparison terms for the coefficients $R_{1,k}$ of the following block are memorized; these are of order i = 1, and the respective block is either assigned to the pre-existing class or used to create a new class, and so forth.

At the end of recording, i.e. after the experiment, the following data are available in the memory:
centers of gravity of the 15 coefficients $R_{j,k}$ ($j \neq 0$) and assignment of each of the sampling blocks to a class.

Then, by well-known mathematical methods, an autoregressive parametric model, of order 15 in the case of calculating 16 standardized correlation coefficients may be generated for each class. One can deduce a frequency spectrum from this model and calculate, for several frequency bands considered particularly significant for assignment to a sleep stage, the percentage of the total energy of the signal contained in the band. Experiment has shown that it is generally convenient to adopt three frequency bands going from 1 to 4 Hz, from 4 to 7 Hz, and from 12 to 14 Hz (this distribution is not however the only possible distribution).

If the percentage of energy for the band of order m (m taking the values 1, 2, and 3) designated by $B_m$, coefficients $c_s$ whose number is equal to that of the previously defined sleep stages, (which are in general those which visual analysis can distinguish) may be computed for each class. These coefficients have the form:

$$c_s = \sum_m a_{m,s} B_m + \beta_s \tag{6}$$

Each of the classes obtained by automatic frequency analysis is then assigned to the sleep stage most likely to be representative of the class Cp. This probability P is given by:

$$P(C_p \in \text{stage } S) = \exp c_s / \sum_S \exp c_s \tag{7}$$

Coefficients $a_{m,s}$ and $\beta_s$ can be determined by statistical analysis of a large number of experiments, exceeding one hundred. In the case considered above of six sleep stages and three frequency bands, the values of Table I were found satisfactory:

TABLE I

| $B_m$ Stages | Bands $a_{m,s}$ | | | $\beta_s$ |
|---|---|---|---|---|
| | 1 to 4 Hz | 4 to 7 Hz | 12 to 14 Hz | |
| Waking | 0.21 | 0.42 | 1.75 | −14.16 |
| Paradoxical sleep | 0.98 | 1.10 | 1.96 | −33.92 |
| Stage 1 | 0.68 | 0.74 | 1.98 | −22.83 |
| Stage 2 | 1.29 | 0.79 | 3.26 | −40.90 |
| Stage 3 | 1.97 | 0.46 | 1.90 | −54.84 |
| Stage 4 | 2.54 | 0.04 | 0.55 | −74.30 |

The values of $a_{m,s}$ can vary by about ±5% in the 1 to 4 Hz band, by ±10% in the 4 to 7 Hz band, and ±15% in the 12 to 14 Hz band. These possibilities of variation take into account observations concerning the greater or lesser significance of the three bands. If only the 1 to 4 Hz band is used, the classification is correct in about 55% of cases. By adding the use of the 4 to 7 Hz band, the classification is improved by 15%. Finally, the use of the 12 to 14 Hz band brings another improvement of about 8%. This simple indication shows that, in certain cases, only two bands can be used. In other cases, if as fine an analysis as possible is desired, a still higher number of frequency bands can be adopted.

Figure 2:
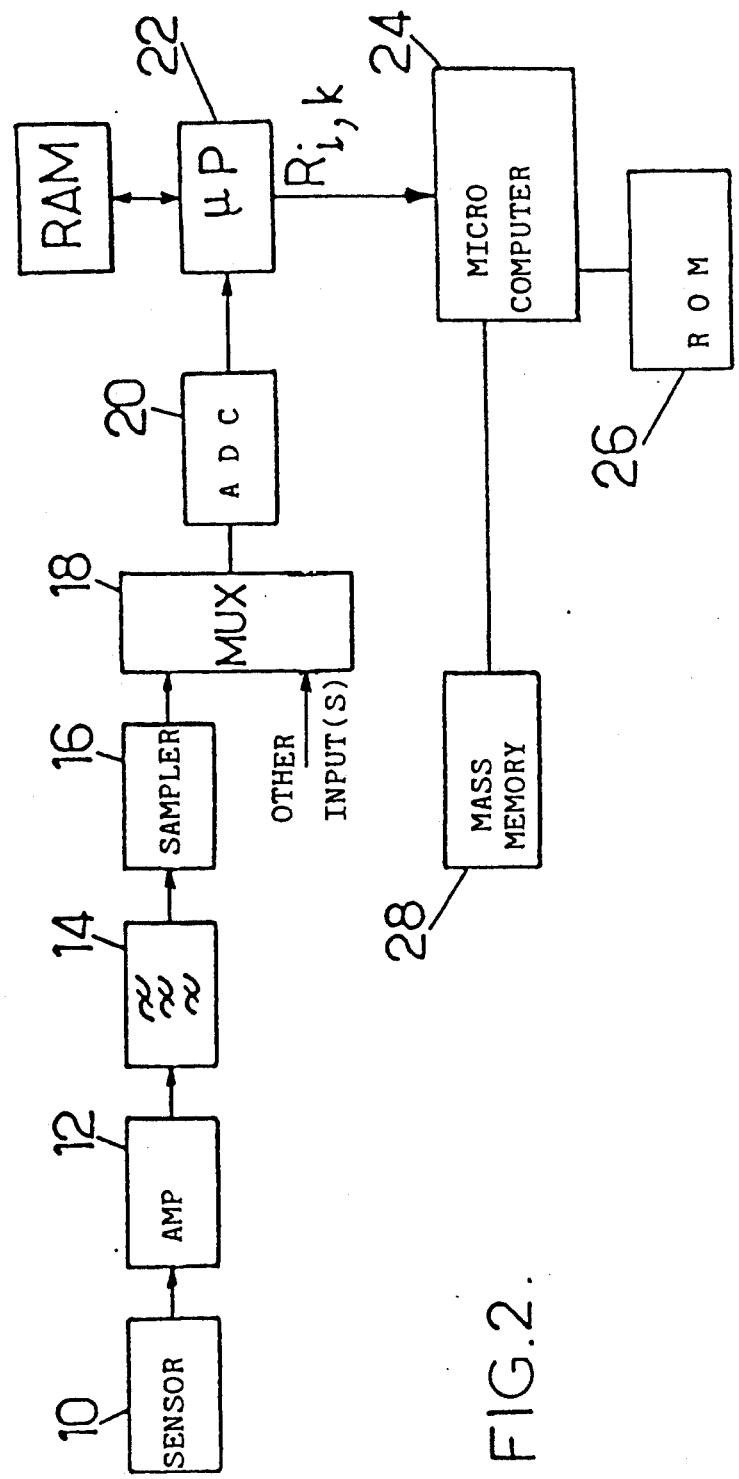
FIG. 2 is a synoptic diagram showing the essential components employed in the system.

The system for implementing the method can have the design shown in FIG. 2. The signal delivered by sensor 10 and amplified at 12, for example in an array of graphic recorders of a conventional type, is applied to an analog passband filter 14, whose passband is between 1 and 40 Hz. The output signal from filter 14 is applied to a 16 to 100 Hz sampler which feeds one of the inputs of a multiplexer 18. It is actually possible to process several EEG signals simultaneously in the same system because of the small amount of calculation necessary. The samples are converted into 12-bit numbers by an analog-digital converter 20 and applied to a 16-bit microprocessor 22 designed to preprocess and transmit the results of this preprocessing, constituted by correlation coefficients, calculated for each 30-second segment, to a microcomputer 24, generally of the personal computer type. Transmission can be effected by an asynchronous RS232 serial link in blocks of 150 8-bit bytes after each 30-second segment. These 150 8-bit bytes also allow additional information such as each block number, the number of saturations, and any calculation overflows, to be transferred.

The classification software can be stored, either in a memory associated with the microprocessor if the latter assumes the function, or in the memory 26 of the microcomputer 24 which stores, in its RAM 28, all the data corresponding to the successive blocks such as, in particular, correlation coefficients R, a block recording file, a class file for each patient, etc. It calculates the coefficients c defined above and the probabilities. As a consequence, it assigns the classes, which are constituted by a self-learning process, to the stages predetermined by the operator, and hence distributes the signal segments between the various stages. Often, the threshold value chosen is such that the number of classes obtained at the end of a night of sleep ranges from 20 to 30, while the number of stages established by EEG specialists is 6, which number represents the maximum practical number of stages between which it is possible to discriminate by visually observing the EEG signal. As a result, intermediate sleep stages can be introduced, noted 1-1, 1-2, ..., 2-3, for example, used whenever none of the probabilities calculated is greater than a predetermined value, 70% for example.

Additional analysis software can be stored in memory 26 of microcomputer 24. This software processes the files and carries out additional operations such as elimination of insignificant classes, required association of a class with a sleep stage, graphic display of results, hypnograms resulting from different classification criteria, etc. Such an analysis allows the operator to intervene to take particular parameters into account, such as the age bracket of the subjects studied, to take into account the substantial change in the EEG signal according to age.

The invention is open to numerous alternative embodiments, particularly regarding the system employed. The various functions may be distributed differently from the manner described, both with regard to the distribution of processing between the analog and the digital parts, and with regard to the assignment of digital processing to the calculation units.

We claim:

1. Device for processing an encephalographic signal and for determining sleep stages during a time period, comprising:
   (a) means for acquiring an EEG signal;
   (b) a sampler and an analog-digital converter for digitally sampling said EEG signal during a plurality of successive EEG signal time segments of a predetermined length and delivering said successive blocks of N samples each corresponding to one of the EEG signal time segments;
   (c) a preprocessing microprocessor programmed to calculate M standardized correlation coefficients $R_{i,k}$ for each of said blocks of said EEG signal, M being an integer smaller than N, and
   (d) a computer for storing said signal blocks and correlation coefficients, and,
   for the first block $i=1$, creating a first EEG signal distribution class defined by the correlation coefficients $R_{1,k}$ of said first block, and
   for each later block i: computing the coefficients $R_{j,k}$ of the centers of gravity of already existing EEG signal distribution class or classes j, calculating distances D(i,j) between the coefficients $R_{i,k}$ of a current block and the coefficients $R_{j,k}$ of the centers of gravity of existing EEG signal distribution classes j, selecting a minimum D(i,p) of the distances D(i,j) and assigning block i to EEG signal distribution class p and updating the center of gravity of the EEG signal distribution class if D(i,p) is less than a given threshold, or creating a new EEG signal distribution class if D(i,p) is greater than said given threshold to automatically classify sleep stages based on energy distribution of said EEG signal distribution classes.

2. Device according to claim 1, wherein said acquiring means includes a filter which has a passband of from 1 to 40 Hz and said sampler has a sampling frequency of 100 Hz.

3. Device according to claim 1, wherein said acquiring means includes a bandpass filter having a predetermined bandpass frequency range and said sampler has a sampling frequency of at least twice an upper limit of the bandpass frequency range.

4. Method for processing an electroencephalographic signal for determining sleep stages during a signal pickup period, comprising the steps of:
   (a) detecting an EEG signal during said pickup period;

(b) dividing the EEG signal into EEG signal time segments having a same predetermining length;

(c) digitally sampling each EEG signal time segment to obtain successive blocks i of N samples of said EEG signal time segments, N being an integer greater than 1;

(d) for each block i, determining M standardized correlation coefficients $R_{i,k}$, with M being an integer smaller than N;

(e) for a first block i=1, storing self-correlation coefficients $R_{1,k}$ as representative of a first EEG signal distribution class and as being centers of gravity for the first class;

(f) for each block i, calculating distances D(i,j) between the coefficients $R_{i,k}$ of a current block and coefficients $R_{j,k}$ of centers of gravity of existing EEG signal distribution classes, said coefficients $R_{j,k}$ being only self-correlation coefficients of the first class for a second block;

(g) selecting a minimum D(i,p) of the distances D(i,j);

(h) assigning block i to an EEG signal distribution class p and updating the center of gravity of class p if D(i,p) is less than a given threshold, or creating a new EEG signal distribution class if D(i,p) is greater than the given threshold; and (i) assigning each EEG signal distribution class to a closest sleep stage based on energy distribution between frequency bands to automatically classify sleep stages based on characteristics of the EEG signal.

5. Method according to claim 4, wherein step (i) includes the steps of:

generating an autoregressive parametric model for each EEG signal distribution class;

deriving a frequency spectrum from said model, computing, for a plurality of frequency bands significant for assignment to a sleep stage, the percentage $B_m$ of the total energy of the signal contained in the band;

computing, for each EEG signal distribution class m, coefficients $c_s$ in a number equal to that of the previously defined sleep stages; and assigning each of the classes obtained by automatic frequency analysis to a sleep stage most likely to be representative of the EEG signal distribution class.

6. Method according to claim 5, wherein said frequency bands consist of three bands of 1 to 4 Hz, 4 to 7 Hz, and 12 to 14 Hz.

* * * * *